United States Patent [19]
Tomasula et al.

[11] Patent Number: 5,925,737
[45] Date of Patent: Jul. 20, 1999

[54] WHEY PROTEIN FRACTIONATION USING HIGH PRESSURE OR SUPERCRITICAL CARBON DIOXIDE

[75] Inventors: Peggy M. Tomasula, Titusville, N.J.; Nicholas Parris, Norristown, Pa.

[73] Assignee: The United States of America as represented by the Secretary of Agriculture, Washington, D.C.

[21] Appl. No.: 08/996,136

[22] Filed: Dec. 22, 1997

[51] Int. Cl.$^6$ .............................. C07K 1/30; C07K 14/76
[52] U.S. Cl. .................... 530/365; 530/366; 530/386; 530/418; 530/419; 530/833
[58] Field of Search .................. 530/340, 366, 530/833, 386, 418, 419

[56] References Cited

U.S. PATENT DOCUMENTS

| | | | |
|---|---|---|---|
| 5,077,067 | 12/1991 | Thibault et al. | 426/271 |
| 5,169,968 | 12/1992 | Rice | 554/193 |
| 5,432,265 | 7/1995 | Tomasula | 530/361 |
| 5,455,331 | 10/1995 | Rice | 530/366 |

OTHER PUBLICATIONS

Parris et al., *J. Agric. Food Chem.*, vol. 38(3), pp. 824–829(1990).

Amundson et al., *Journal of Food Processing and Preservation*, vol. 6(2), pp. 55–71(1981).

Slack et al., *Journal of Food Processing and Preservation*, vol. 10(1), pp. 19–30(1985).

Kuwata et al., *Journal of Food Science*, vol. 50, pp. 605–609(1985).

Mashikh et al., *Journal of Food Science*, vol. 52, pp. 1236–1240(1987).

Tomasula et al., *Journal of Dairy Science*, vol. 78(3), pp. 506–514(1995).

Tomasula et al., Abstract; 1995 International Chemical Congress of Pacific Basin Societies; Dec. 17–22, 1995.

*Primary Examiner*—Cecilia J. Tsang
*Assistant Examiner*—Fabian A. Jamelson
*Attorney, Agent, or Firm*—M. Howard Silverstein; John D. Fado; Janelle S. Graeter

[57] ABSTRACT

A process for the fractionation of proteins from an aqueous solution of whey is described. The process includes mixing the solution with carbon dioxide under pressure, heating the mixture to increase the pressure, releasing the pressure and lowering the temperature of the mixture, then separating a supernatant liquor from a precipitate which results from the process.

25 Claims, 2 Drawing Sheets

WHEY PROTEIN FRACTIONATION USING HIGH PRESSURE OR SUPERCRITICAL CARBON DIOXIDE

BACKGROUND OF THE INVENTION

1. Field of the Invention.

Current processes for the fractionation of whey proteins that rely on the addition of chemical agents result in contamination of the proteins, requiring additional steps to remove the contaminants. These chemicals can have an adverse effect on protein functional behavior and its ultimate use in food products. This invention relates to a process for fractionating whey proteins with high pressure $CO_2$ or supercritical $CO_2$.

2. Description of the Related Art.

Sweet whey, a watery by-product of the cheese manufacturing process, comprises almost 7% solids. Proteins account for about 10–12% of the solids content, the rest being mainly lactose, minerals, milkfat and lactic acid at 74%, 8%, 3% and 3%, respectively (Morr, D. V. 1989. In: *Developments in Dairy Chemistry*—4. Fox, P. F. ed., Elsevier Applied Science, New York.) With the advent of ultrafiltration, whey protein concentrates (WPC) ranging from 35 to 85% protein content have been obtained. Depending on protein content, these concentrates have properties such as good solubility, emulsification, water binding, foam formation and gelation, and because of their nutritional properties, they are useful for protein fortification. The functionality generally improves as the protein content increases. For example, WPC with lower protein content are best for protein fortification while those of higher protein content impart texture and gelling properties.

The proteins, α-lactalbumin (α-La), β-lactoglobulin (β-Lg), bovine serum albumin (BSA), and heavy and light chain immunoglobulins (Ig) comprise the principal whey proteins. Whey also contains minor proteins such as lactoferrins (Lf), proteose peptide components, glycomacropeptides and low molecular weight enzymatic degradation products of the caseins (DeWit, J. N. 1989. In: *Developments in Dairy Chemistry*—4. Fox, P. F., ed. Elsevier Applied Science, NY). The properties of the β-Lg fraction are desirable in binding and gelation, and the α-La fraction may find use in humanized infant formulas (Heine et al., WO 92/03468, Mar. 5, 1992).

Many methods have been reported for fractionation of the whey proteins into α-La and β-Lg enriched fractions. These methods generally rely on gentle heat treatment and pH adjustment (Pearce, R. J. 1983. *Australian J. Dairy Technol.* vol. 38, p. 144; Pearce, R. J. 1987. *Australian J. Dairy Technol.* vol. 212, p. 150; Pearce et al. 1991. *Food Res. Quarterly.* vol. 51, p. 137), addition of salts (Aschaffenburg and Drewry. 1957. *Biochem J.* vol. 65, p. 273; Kaneko et al. 1985. *J. Food Sci.* vol. 50, p. 1531; Kuwata et al. 1985. *J. Food Sci.* vol. 50, p. 605; Al-Mashikh and Nakai. 1987. *J. Food Sci.* vol. 52, p. 1237; Maillart and Ribadeau-Dumas. 1988. *J. Food Sci.* vol. 53, p. 743; Mate and Krochta. 1994. *J. Food Sci.* vol. 59, pp. 1111–1113), separation using a PEG/potassium phosphate aqueous two-phase system (Chen, J. 1992. *J. Ferment. Bioeng.* vol. 73, p. 140), extraction with organic solvents (Heine, supra), microfiltration (Uchida, T. EP 0 556 083, Jan. 28, 1993), anion exchange (Venter, B. G. 1984. *S. Afr. J. Dairy Technol.* vol. 16, p. 79; Thibault. P. A., U.S. Pat. No. 5,077,067, 1991), cation exchange (Ohtomo et al. 1988. *Japanese Soc. Food Sci. Technol.* vol. 35, pp. 755–762), ultrafiltration (Roger et al. U.S. Pat. No. 4,711,953, 1987), various chromatographic methods (Biscans et al. 1985. *Entropie N°.* vol. 21, p. 17; Chiancone and Gattoni. 1993. *Biotechnol. Appl. Biochem.* vol. 18, pp. 1–8; Carrere et al. 1994. *Trans IchemE.* vol. 72, p. 216), or techniques using ultrafiltration and electrodialysis (Amundson and Watanawanichakorn. 1982. *J. Food Proc. and Preserv.* vol. 6, p. 55; Slack et al. 1986. *J. Food Proc. and Preserv.* vol. 10, p. 19). Preliminary experiments utilizing carbon dioxide were also reported by Tomasula et al. (1995. International Chemical Congress of Pacific Basin Societies, Honolulu, Hi.).

SUMMARY OF THE INVENTION

We have discovered a process wherein solutions containing whey proteins, such as whey protein concentrates (WPC) are contacted with high pressure or supercritical carbon dioxide ($CO_2$) to fractionate α-La and β-Lg. The fractionation process may be carried out using an aqueous solution of whey, and the method comprises a) mixing the solution with $CO_2$ under pressure, b) heating the mixture, thereby increasing the pressure, c) releasing the pressure and lowering the temperature of the mixture and d) separating the resulting precipitate from the slurry. Alternatively, steps a) and b) may be reversed, such that step a) is heating the solution and step b) is mixing the solution with $CO_2$ under pressure.

In a preferred process, the method comprises a) introducing an aqueous whey solution into a reaction vessel capable of withstanding elevated pressures, b) admitting $CO_2$ into said reaction vessel until a predetermined fill pressure $P_1$ is attained, c) heating the contents of the vessel to a predetermined temperature $T_1$, whereby the pressure therein is increased to a new level $P_2$, d) maintaining the temperature and pressure for a predetermined time, e) releasing said pressure and lowering said temperature to a new level $T_2$, f) maintaining the vessel contents at $T_2$ for a second predetermined time, and g) separating the resulting precipitate from the supernatant liquor by any conventional separation means. Alternatively, steps b) and c) may be reversed, such that step b) is heating the contents of said reaction vessel to a predetermined temperature $T_1$, whereby a pressure $P_1$ is achieved, and step c) is admitting $CO_2$ into the vessel until a predetermined pressure $P_2$ is attained.

In a more preferred process, an aqueous solution containing from about 7% to about 25%(w/w) whey is utilized in a method comprising a) introducing the solution into a reaction vessel capable of withstanding elevated pressures substantially in excess of 2760 kPa, b) closing said reaction vessel, c) admitting carbon dioxide into said closed reaction vessel until a fill pressure of at least about 2760 kPa is attained, d) heating the contents of the vessel to a temperature in the range of from about 54° C. to about 64° C., whereby the pressure therein is increased, e) maintaining said temperature and pressure for at least about 10 minutes, f) releasing said pressure and lowering said temperature to a temperature sufficient for cooling, i.e. up to about 45° C., g) maintaining the vessel contents at the lower temperature for a time sufficient for the mixture to cool, and h) separating the resulting precipitate from the supernatant liquor by centrifugation or microfiltration. Alternatively, steps c) and d) may be reversed, such that step c) is heating the contents of the closed reaction vessel to a temperature in the range of from about 54° C. to about 64° C. and step d) is admitting $CO_2$ into the vessel until a fill pressure of at least about 2760 kPa is attained.

DETAILED DESCRIPTION OF THE INVENTION

Figure 1:
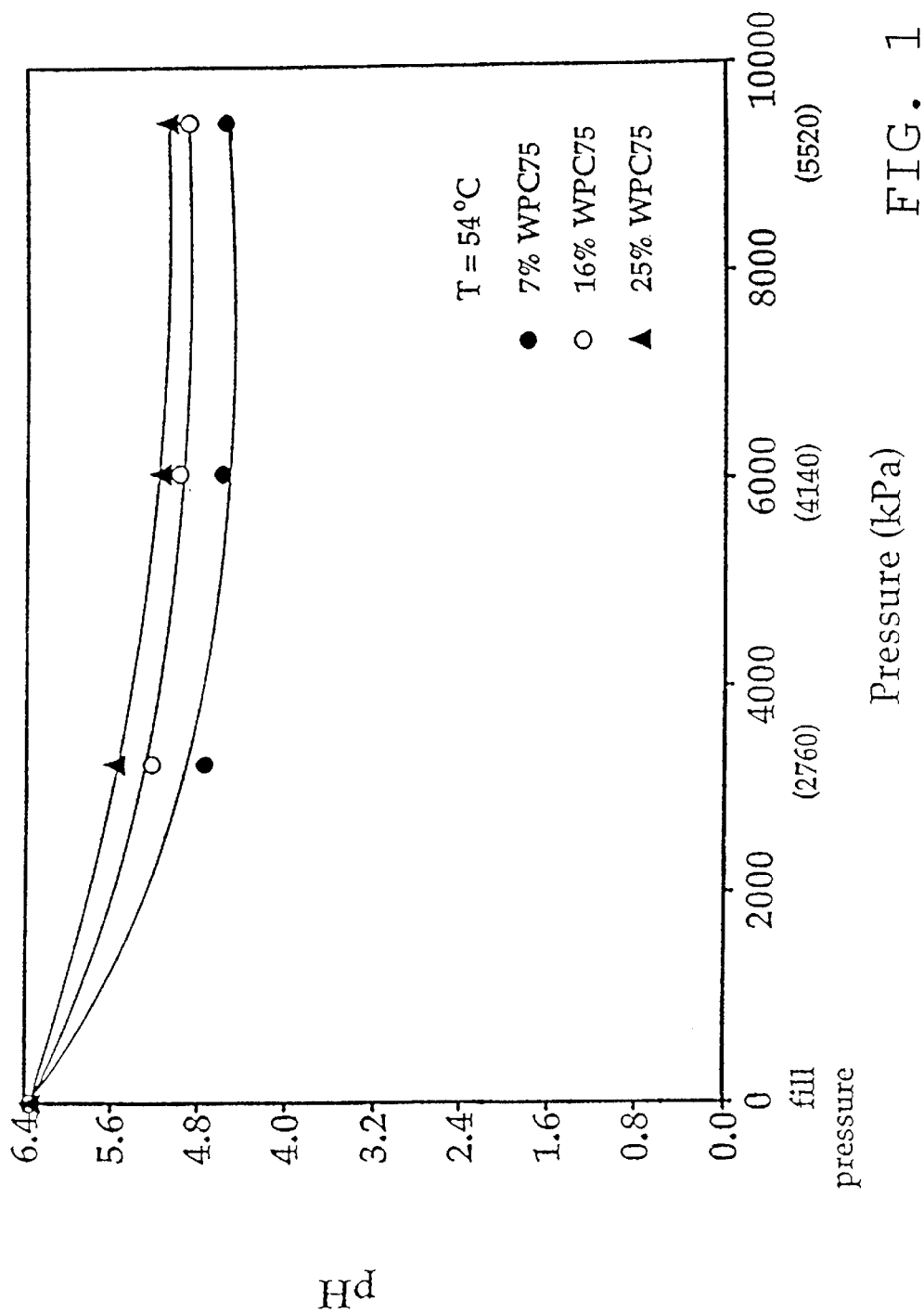
FIG. 1 shows pH as a function of pressure for 7%, 16% and 25% WPC solutions at 54° C.

The fractionation process is carried out on whey protein-containing solutions (e.g. WPC) which are contacted with high pressure or supercritical $CO_2$ to fractionate the proteins α-La and β-Lg. The process may be carried out batchwise or continuously. An effective continuous process is described in Tomasula, P. M., U.S. Pat. No. 5,432,265, 1995, herein incorporated by reference.

The starting material for the process of the invention is an aqueous solution of whey. This material may be obtained by dilution of a commercially available whey protein concentrate, such as, 75% whey protein concentrate (WPC75) obtained from Calpro Ingredients, Inc. (Corona, Calif.). Any desired level of dilution can be employed. Levels ranging from about 7% to about 25% (w/w) have been found convenient and are preferred. The use of a 7% solution has been found optimal from the standpoint of the best fractionation of the proteins and is the most preferred.

Carbon dioxide is added to the solution to a pressure of at least about 2760 kPa to form carbonic acid ($H_2CO_3$). Increasing the pressure of the $CO_2$ injected into the whey solution results in an increased production of hydrogen ions, thereby lowering the pH. Precipitation of a portion of the protein present in the solution then occurs, which may in part be due to the lower pH. Therefore, increasing pressure is desirable in the practice of the invention. It has been found that below about 2760 kPa, no precipitate is formed. Those skilled in the art will readily understand, however, that an upper limit is imposed, as a practical matter, by the pressure limits of the particular equipment employed.

The mixture is then heated to a temperature in the range of from about 50° C. to about 65° C., held briefly, then depressurized to atmospheric pressure and cooled. It has been found that below 50° C., no precipitate is formed and that above 65° C., the protein begins to denature. Preferred temperatures are therefore in the range of from about 54° C. to about 64° C.

The extent of time that the mixture is held at the elevated temperature may vary. Times of from about 5 minutes up to about 30 minutes have been found useful and practical, although at 5 minutes, one obtains only about half as much precipitate as at 30 minutes. In practice, it is preferred that the time held at the elevated temperature be in the range of from about 10 minutes to about 20 minutes, as this represents an optimization between time and yield.

The degree to which the heated and depressurized reaction mixture is cooled may also vary and is not critical to the process. Successful experiments have been carried out where the temperature was lowered to 10° C., as well as to 45° C. Lowering the temperature into the range of from about 10° C. to room temperature, i.e. about 20° C., is preferred. It has been found convenient to maintain the lowered temperature for about 15 minutes, although reasonable variations would not be found harmful.

At this stage of the process, the contents of the reaction vessel are in the form of a slurry comprising a water-insoluble precipitate and a supernatant liquor. The precipitate, the α-La fraction, comprises, depending upon reaction conditions, on average about 55% α-La by weight. The remaining 45% comprises, inter alia, lipoproteins, minor proteins and enzymes. The supernatant liquor, the β-Lg fraction, comprises about 78% β-Lg by weight. Separation of the two phases can be accomplished by any of the conventional separation means known to those of skill in the art, e.g. decantation, filtration, centrifugation and the like.

Although the reaction pH is on the order of about 4 during the pressurized reaction, the final solution pH is about 6.3. This change in pH occurs because the acidic $H_2CO_3$ is converted back to $CO_2$ when the pressure is released, the $CO_2$ then venting into the atmosphere. In the mineral acid precipitation processes described in the prior art, on the other hand, the final pH is about 4.6, and neutralization is generally required, resulting in the formation of salts which must subsequently be removed.

The fractionation process is thus advantageous in that no pH adjustment is necessary after fractionation, no additional minerals and/or ions are added, proteins are not chemically or thermally denatured, there is no contamination from completing agents and large volumes of material can be processed at once. In addition, the process results in products which are useful in a variety of new ingredient markets. The food and pharmaceutical industries utilize the individual protein properties of WPC, the gelling properties of β-Lg and the emulsifying properties of α-La. α-La is also useful in special diets and as a stabilizer for dairy mixtures. β-Lg contributes functional properties to edible products, such as films and dairy surimi, acts as a binder with properties similar to egg proteins and in fortification-functional properties lacking in WPC.

α-La is also useful in humanized infant formulations in place of WPC eliminating β-Lg, which can act as an allergen. More specifically, infant formulas are often manufactured from proteins extracted from cow's milk. In order to resemble human milk, a special formulation of the different ingredients of cow's milk is necessary. For example, the provision of essential amino acids provided by the formula must be as close as possible to that provided by the proteins of human milk. Further, cow's milk contains more casein in proportion to whey than does human milk, the casein/whey ratio of the former being 79/21 and the latter, 40/60.

Accordingly, it is necessary to shift the balance of the whey protein/casein ratio in cow's milk in favor of the whey proteins, e.g. raising the whey content by addition of WPC. This has proven problematic, however, since the whey from cow's milk does not have the same composition as the whey in human milk: there is no more than a trace of β-Lg in human milk, but a substantial amount in cow's milk. This excess of β-Lg in a cow's milk-based formulation can cause gastrointestinal disorders in some infants. A number of means for eliminating the β-Lg have been suggested in the art, and the process described herein provides an additional means whereby reduction of β-Lg can be accomplished.

The following example is intended to further illustrate the invention and is not intended to limit the scope of the invention as defined by the claims.

EXAMPLE

Fractionation Method
1. Starting Materials and Equipment.

Whey solutions were prepared from 75% whey protein concentrate (WPC75) obtained from Calpro Ingredients, Inc. (Corona, Calif.). The nominal analysis supplied by the manufacturer for Lot #3113TA was as follows: protein, 78.9%; moisture, 3.4%; fat, 7.1%; ash, 2.3%; lactose by difference, 8.3%. An analysis was also performed in the laboratory before use, resulting in values of: protein, 77.4%; moisture, 4.7%; fat, 6.5%; ash, 2.7%; lactose by difference, 8.8%.

A 1000 mL Model 4521 316SS Parr batch reactor (Parr Instrument Co., Moline, Ill.) was used for the fractionation of the WPC75 solutions into α-La and β-Lg fractions. A detailed description of the construction and use of the reactor is found in Tomasula et al. 1995. *J. Dairy Sci.* vol. 78, pp. 506–514, herein incorporated by reference.

2. Preliminary Studies.

Experiments were conducted using 750-gram samples of 7%(w/w) and 25%(w/w) WPC75 solutions prepared with triple-distilled water to establish the minimum temperature, pressure and reactor residence time required for precipitation of the α-La fraction.

In a typical trial, a diluted WPC75 solution refrigerated at 6° C. was poured into the batch reactor and the lid secured. Carbon dioxide (AirCo., BOC Group, Murray Hill, N.J.) was allowed to fill the reactor until fill pressures of 2760 kPa, 4140 kPa or 5520 kPa were reached. The contents of the reactor were then rapidly heated to the desired temperature, thereby increasing the pressure. The reactor contents were held for a residence time of up to 30 min. Pressure was then released and the reactor contents cooled to 10° C. and held there for 15 min. The resulting slurries were centrifuged using a Model RC-5B Sorvall Refrigerated Superspeed Centrifuge (Newtown, Conn.) at approximately 5000 g for 1 hr.

The precipitate was freeze dried, and the extent of precipitation of the α-La enriched fraction was estimated by dividing the weight of precipitate by the weight of protein in the initial WPC sample on a dry basis. Precipitates were obtained only at temperatures greater than 50° C. and at pressures greater than 2760 kPa. Half as much precipitate was formed at a residence time of 5 min as compared to 30 min. The yield of precipitate was the same at 10 as at 20 min.

Experiments were not conducted above 64° C. because the pressure limits of the vessel would have been exceeded by heating the $CO_2$-WPC75 solutions to higher temperatures. In addition, denaturation of the proteins occurs at temperatures greater than 65° C. (Pearce, R. J., 1983, supra).

Additional trials were conducted using solutions with total solids contents greater than 25%(w/w), but the precipitates were difficult to remove at the low speed used for centrifugation because of the solution viscosity. Thus, 25% (w/w) became the practical upper limit for total solids.

For the experimental trials, 750 g of 7%(w/w), 16%(w/w) or 25%(w/w) solutions were used. In a typical trial, the reactor was filled with $CO_2$ until a pressure of 2760 kPa, 4140 kPa or 5520 kPa was reached. The reactor contents were then heated to 54° C., 60° C. or 64° C. and held for a residence time of 10 min. The reactor was then depressurized, and the reactor contents were cooled to either 10° C. or 45° C. and held for 15 min.

The extent of precipitation of the α-La fraction was estimated by dividing the weight of precipitate by the weight of protein in the initial WPC sample. Experiments were performed in triplicate, and the data were analyzed by ANOVA.

The samples were not purified. The precipitated α-La enriched fraction was washed thoroughly with distilled water and then freeze fried. The β-Lg fraction was not treated further.

3. Analytical Methods and pH Measurement.

The procedures described by Tomasula et al., supra, were followed for the determination of solids, ash and calcium. Fat content was obtained by the Roese-Gottlieb method (AOAC 16.064), and protein content was obtained by the Kjeldahl method (AOAC 16.213) using a factor of 6.38. Lactose content was obtained by difference.

pH values were measured with a high-pressure probe (Innovative Sensors, Inc., Anaheim, Calif.) designed to withstand pressures up to 6.9 Mpa, with probe placement as described in Tomasula et al., supra.

4. Determination of Whey Proteins.

Sodium dodecyl sulfate-polyacrylamide gel electrophoresis (SDS-PAGE) of protein samples was carried out on a Phast System (Pharmacia, Piscataway, N.J.) with a Phast gel gradient of 8–25% acrylamide. Samples were prepared and proteins separated according to the method of Parris et al. (1990. *J. Agr. Food Chem.* vol. 35, p. 824). The protein bands were stained with Coomassie R350 dye. Molecular weight standards were run with WPC75 (Calpro Ingredients, Inc., supra). The stained gels were dried and the intensity of the bands scanned with ImageQuaNT™ (Molecular Dynamics, Inc., Sunnyvale, Calif.). The coefficient of variation for α-La and β-Lg in 5 replicate whey samples using this method were 11.9% and 9.1%, respectively.

5. Results.

Preliminary runs showed that very small amounts of precipitate were obtained at temperatures less than 54° C. and at fill pressures of less than 2760 kPa. Aggregation of α-La occurred under the conditions of temperature (54° C.$\leq T \leq$64° C.), fill pressure (2760 kPa$\leq P \leq$5520 kPa), concentration (7%,w/w$\leq C \leq$25%,w/w) and residence time (10 min$\leq t \leq$30 min). The corresponding β-Lg solutions were mostly clear, although some retained a haze after precipitation.

Figure 2:
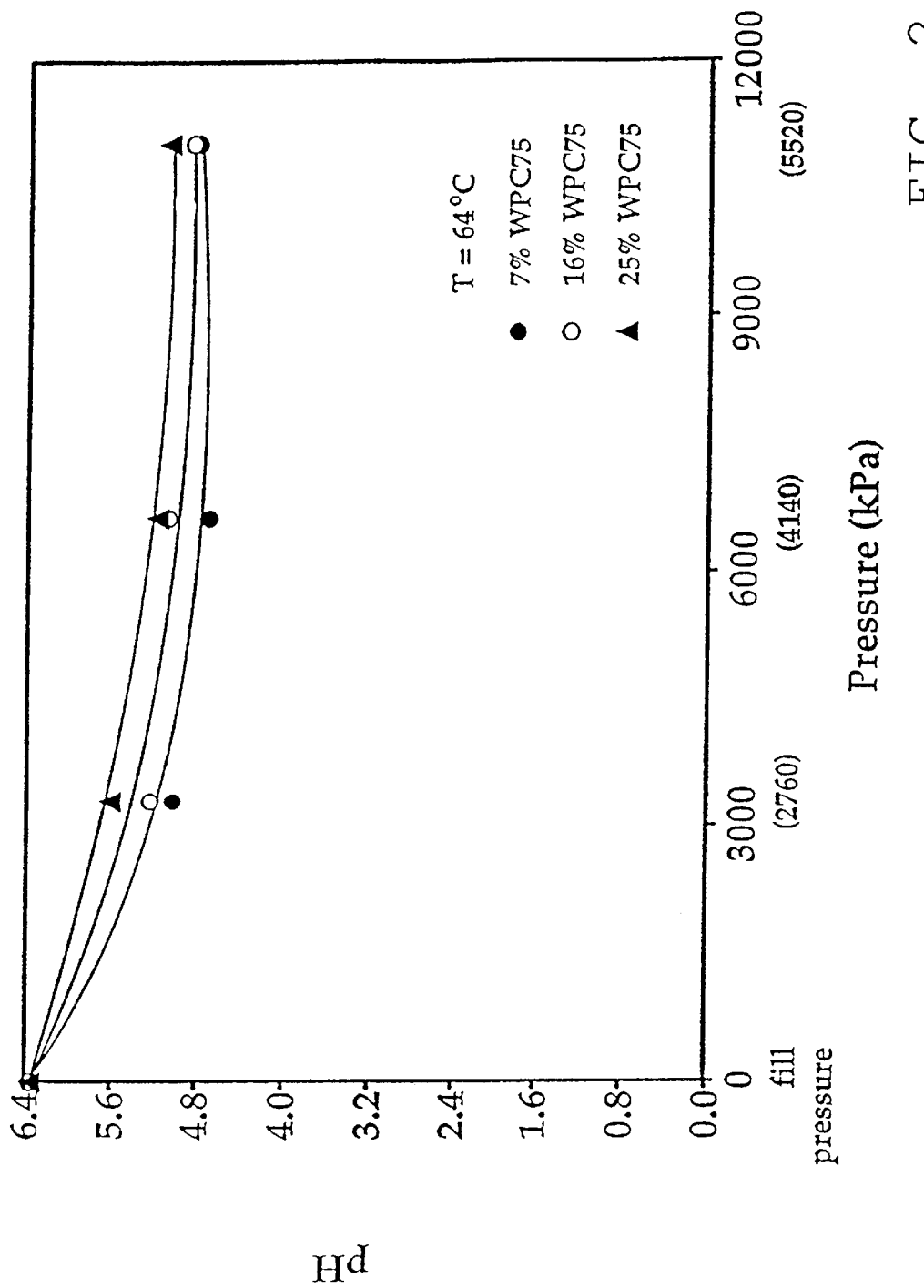
FIG. 2 shows pH as a function of pressure for 7%, 16% and 25% WPC solutions at 64° C.

The effects of $CO_2$ pressure on the corresponding precipitation pH obtained after heating the vessel to 54° C. or 64° C., respectively, are shown in FIGS. 1 and 2, with fill pressures shown in parentheses. The results for 60° C. are not shown.

pH decreases dramatically with increasing pressure up to 2760 kPa. From 2760 kPa to 4140 kPa for the 7% WPC solution, the decrease is only on the order of about 0.2 pH units. Increasing pressure further from 4140 kPa to 5520 kPa does not significantly decrease pH. Although not shown in the figures, the original pH is restored after the depressurization step in the process. This is a significant advantage because bases such as KOH or NaOH do not have to be added to the solution for neutralization. A comparison of FIGS. 1 and 2 shows that the pHs at the two temperatures do not differ greatly, indicating that pH effects under these conditions are approximately the same.

The total amount of α-La precipitate formed does not differ significantly with changes in pressure (or pH) or temperature. This is apparent from FIGS. 1 and 2, which show that increases in pressure do not correlate with significant differences in pH.

6. Composition of the Precipitates.

Compositions of the α-La- and β-Lg enriched fractions are in Table 1. Results are shown for the 7% WPC75 solutions only.

The fat content in the α-La fraction was greater than in the β-Lg fraction. After centrifugation of the α-La precipitate/β-Lg supernatant mixture, a distinct fat layer was

TABLE 1

Effect of Temperature and Presssure on the Composition of the α-La and β-Lg Whey Protein Fractions from 7% (w/w) WPC75. Moisture-free Basis[1].

| TC | P | % TS | % Ash | % Protein | % Fat | % Lac | % Calcium[2] |
|----|------|------|---------|-----------|-------|-------|------------|
| 54 | 2760 | 7 | α 0.93 | 83.3 | 10.6 | 5.2 | 14.7 |
|    |      |   | β 3.60 | 87.9 | 2.8 | 5.7 | 85.3 |
| 54 | 4140 | 7 | α 1.93 | 75.0 | 11.1 | 12.0 | 41.0 |
|    |      |   | β 2.71 | 90.3 | 0.8 | 6.2 | 59.0 |
| 54 | 5520 | 7 | α 1.82 | 78.8 | 11.8 | 7.6 | 59.9 |
|    |      |   | β 2.97 | 88.5 | 0.1 | 8.5 | 40.9 |
| 64 | 2760 | 7 | α 1.04 | 85.9 | 9.0 | 4.1 | 28.7 |
|    |      |   | β 3.60 | 78.7 | 3.1 | 14.6 | 71.3 |
| 64 | 4140 | 7 | α 1.09 | 88.2 | 8.6 | 2.2 | 24.4 |
|    |      |   | β 3.59 | 77.4 | 3.1 | 15.7 | 73.7 |

TABLE 1-continued

Effect of Temperature and Presssure on the Composition of the α-La and β-Lg Whey Protein Fractions from 7% (w/w) WPC75. Moisture-free Basis[1].

| TC | P | % TS | % Ash | % Protein | % Fat | % Lac | % Calcium[2] |
|----|------|------|----------------|-----------|-----------|-----------|--------------|
| 64 | 5520 | 7    | α 1.21<br>β 3.13 | 85.2<br>87.4 | 8.4<br>3.3 | 5.2<br>6.2 | 58.0<br>41.8 |

[1]Average of three values.
[2]% Calcium calculated relative to amount of calcium in initial 7% WPC75 solution.

observed throughout the supernatant. Amundson et al. (1982. *J. Food Proc. Pres.* vol. 6, pp. 55–71) reported that the ability of β-Lg to hold lipid may be a result of reaction of β-Lg with lipid. Fauquant et al. (1985. *Le Lait*. vol. 65, pp. 1–20) have shown that the residual fat layer in WPC consists mostly of phospholipids which can be removed prior to processing. Table 1 shows that the α-La fraction has a lower fat content at 64° C. than at 54° C. This suggests a possible expulsion of the phospholipid, which is larger than the whey proteins, with aggregate formation and possibly interaction with β-Lg, or an aggregation of the lipids and calcium caused by heat. The fat was not removed prior to processing in this study. Although this fat was not removed in these experiments and could not be removed by centrifugation, Maubois et al. (1987. *Bulletin of IDF*. no. 212, p. 154) as well as Fauquant et al., supra, have shown that this residual fat layer consists mostly of phospholipids and can be removed from WPC prior to processing. There is a decrease in the amount of fat in the α-La fraction as temperature is increased, and apparently an increase in the phospholipid layer as well.

No pressure effect is observed on the ash content of the α-La enriched fractions at either 54° C. or 64° C., but the % ash contents at 54° C. are greater than those at 64° C. The increase in %ash content of α-La with increase in pressure follows the increase in calcium discussed below.

At 54° C., calcium content of the enriched α-La fraction was lowest at 2760 kPa and increased with increasing pressure. At 64° C., the calcium content of the same fraction increased when pressure was increased to 5520 kPa. These results contradict the findings of Hiraoka et al. (1980. *Biochem. Biophys. Res. Comm.* vol. 95, pp. 1098–1104), Kronman et al. (1981. *J. Biol. Chem.* vol. 256, pp. 8582–8587) and Bernal and Jelen (1985. *J. Dairy Sci.* vol. 67, pp. 2452–2454). Aggregation of α-La at the temperatures and pressures (or pH) should be accompanied by a loss in calcium, and further washing may remove excess calcium.

In most cases, %lactose content of the β-Lg fractions is greater than that for the α-La fractions. It should be easily removed from the β-Lg fraction by further processing, such as ultrafiltration.

Increasing temperature resulted in slightly greater increases in protein content of the α-La fraction because of increased precipitation. Increasing pressure resulted in less precipitate at 54° C. and almost no change in amount of precipitate at 64° C.

7. Gel Electrophoresis of Whey Protein Fractions.

While the influence of the temperature and pressure (or pH) on the amount of precipitate or the composition of the enriched fractions is not apparent, its effect on the degree of protein fractionation is, as determined by gel electrophoresis. The results for temperature effects at 4140 kPa are reported in Table 2 as percentage yield or recovery. Recovery is defined as the amount of the whey protein in the enriched fraction divided by the amount in the initial protein. The distribution of the individual whey proteins in the feed WPC75 is also given.

Table 2 shows that the percentage of α-La in the α-La enriched fraction increased with increase in temperature, while the percentages of β-Lg, BSA and Ig decreased. At 54° C., lactoferrin was not detected in the α-La enriched fraction. β-Lg was enriched in the β-Lg enriched fraction with increasing temperature.

TABLE 2

Effect of Temperature and Pressure on Distribution of Whey Proteins in the α-La and β-Lg Enriched Fractions Precipitated from 7% WPC75 Solutions at 2120 kPA

|          |        | 54° C. |       | 64° C. |       |
|----------|--------|--------|-------|--------|-------|
| Fraction | Calpro | α      | β     | α      | β     |
| α-La     | 22.4   | 27.5   | 72.5  | 55.4   | 44.6  |
| β-Lg     | 50.8   | 30.1   | 69.9  | 21.8   | 78.2  |
| BSA      | 9.9    | 63.5   | 36.5  | 55.6   | 44.4  |
| Ig       | 9.5    | 69.4   | 30.6  | 49.4   | 50.6  |
| Lf       | 7.3    | —      | 100.0 | 47.9   | 52.1  |

At a fixed temperature, and a concentration of either 7%(w/w), 16%(w/w) or 25%(w/w), the effect of pressure (or pH) on the degree of fractionation was negligible at the three pressures studied. This is because pH, as shown in the figures, either changes slowly, or the change is insignificant, with a pressure increase of from 2760 kPa to 5520 kPa. For the 7%(w/w) solution at 64° C., the percentage of β-Lg in the β-Lg enriched fraction with respect to total protein, was approximately 78% at the three pressures. The percentage of α-La or β-Lg recovered in either fraction at 16%(w/w) and 25%(w/w) did not improve with the increase in WPC75 feed concentration.

Protein recovery obtained in this study is compared to that obtained in other studies in Table 3. The greatest recovery was obtained using conventional salting methods known in the art, but these methods have the disadvantage of contaminating the protein fractions with salt. Column methods are generally not acceptable for processing large amounts of sample. The results obtained by the process of the present invention are similar to those reported by Pearce, 1987, supra.

TABLE 3

Comparison of β-Lg Recovered by Different Methods

| Method | Recovery β-Lg (%) | Reference |
|--------|-------------------|-----------|
| Salting-out | >99 | Kuwata et al., 1985 |
| Salting-out | 90 | Kaneko et al., 1985 |
| Salting-out | 84 | Maillart and Ribadeau-Dumas, 1988 |
| Salting-out | >65 | Mate and Krochta, 1994 |
| Salting-out | 80 | Al-Masheik and Nakai, 1987 |
| Ultrafiltration and Electrodialysis | 90 | Slack et al., 1986 |
| pH | >75 | Pearce et al., 1991 |
| $CO_2$ | 78 | Tomasula and Parris (Invention) |

While various embodiments of the present invention have been described hereinabove, it is understood that they have been presented by way of example only and not limitation. Thus, the breadth and scope of the invention should not be limited by any of the above-described exemplary embodiments, but should be defined only in accordance with the following claims and their equivalents.

We claim:

1. A process for the fractionation of proteins from an aqueous solution of whey, said process comprising
   a) forming a mixture of said whey solution and carbon dioxide by first, mixing said whey solution with carbon dioxide under pressure and second, heating said mixture, thereby increasing the pressure; or first, heating said whey solution and second, adding carbon dioxide under pressure to the heated whey solution,
   b) releasing the pressure and lowering the temperature of the mixture, and
   c) separating resulting precipitate from the supernatant liquor.

2. The process of claim 1 wherein the proteins comprise β-lactoglobulin and α-lactalbumin.

3. The process of claim 1 wherein the whey is present in the solution at a concentration of from about 7% (w/w) to about 25% (w/w).

4. The process of claim 1 wherein the pressure in step a) is at least about 2760 kPa.

5. The process of claim 1 wherein the mixture in step a) is heated to a temperature in the range of from about 50° C. to about 65° C.

6. The process of claim 5 wherein the temperature is in the range of from about 54° C. to about 64° C.

7. The process of claim 1 wherein the temperature of the mixture in step b) is lowered to a temperature of from about 10° C. to about 45° C.

8. The process of claim 1 wherein the precipitate is separated from the supernatant liquor by centrifugation or microfiltration.

9. The process of claim 1 wherein said process is a batch process.

10. The process of claim 1 wherein said process is a continuous process.

11. A process for the fractionation of proteins from an aqueous solution of whey, said process comprising
    a) introducing said whey solution into a reaction vessel capable of withstanding elevated pressures,
    b) forming a mixture of said whey solution and carbon dioxide by first, admitting carbon dioxide into said reaction vessel until a predetermined fill pressure $P_1$ is attained, and second, heating the contents of the vessel to a predetermined temperature $T_1$, whereby the pressure therein is increased to a new level $P_2$; or by first heating the contents of the vessel to a predetermined temperature $T_1$, thereby attaining an initial pressure $P_1$, and second, admitting carbon dioxide into said reaction vessel, whereby the pressure is increased to a new level $P_2$,
    c) maintaining the temperature and pressure for a predetermined time,
    d) releasing said pressure, and
    e) separating the resulting precipitate from the supernatant liquor.

12. The process of claim 11 wherein the proteins comprise β-lactoglobulin and α-lactalbumin.

13. The process of claim 11 wherein the solution of whey is in a concentration range of from about 7% (w/w) to about 25% (w/w).

14. The process of claim 11 wherein $P_1$ is at least about 2760 kPa.

15. The process of claim 11 wherein $T_1$ is a temperature in the range of from about 50° C. to about 65° C.

16. The process of claim 15 wherein $T_1$ is a temperature in the range of from about 54° C. to about 64° C.

17. The process of claim 11 wherein the temperature and pressure in step c) are maintained for a period of time of at least about 5 minutes to about 30 minutes.

18. The process of claim 17 wherein the period of time is from about 10 minutes to about 20 minutes.

19. The process of claim 11 wherein at step d), the temperature is lowered to a new level $T_2$ and vessel contents are maintained at said temperature for a time sufficient for said contents to cool.

20. The process of claim 19 wherein $T_2$ is a temperature in the range of from about 10° C. to about 45° C.

21. The process of claim 19 wherein $T_2$ in step e) is maintained for about 15 minutes.

22. The process of claim 11 wherein the precipitate is separated from the supernatant liquor by centrifugation or microfiltration.

23. The process of claim 11 wherein said process is a batch process.

24. The process of claim 11 wherein said process is a continuous process.

25. A process for the fractionation of whey proteins into β-lactoglobulin and α-lactalbumin enriched fractions, wherein the whey proteins are present in a solution at a concentration of from about 7% (w/w) to about 25% (w/w), said process comprising
    a) introducing said solution into a reaction vessel capable of withstanding elevated pressures substantially in excess of 2760 pKa,
    b) closing said reaction vessel,
    c) forming a mixture of said solution and carbon dioxide by first, admitting carbon dioxide into said closed reaction vessel until a fill pressure of at least about 2760 kPa is attained, and second, heating the contents of the vessel to a temperature in the range of from about 54° C. to about 64° C., whereby the pressure therein is increased, or first, heating the content of the vessel to a temperature in the range of from about 54° C. to about 64° C., whereby the pressure therein is increased, and second, admitting carbon dioxide into said closed reaction vessel until a fill pressure of at least about 2760 kPa is attained,
    d) maintaining said temperature and pressure for a period of time from about 10 minutes to about 20 minutes,
    e) releasing said pressure and lowering said temperature to a temperature of from about 10° C. to about 45° C.,
    f) maintaining the vessel contents at a temperature of from about 10° C. to about 45° C. for about 15 minutes, and
    g) separating the resulting precipitate from the supernatant liquor by centrifugation or microfiltration.

* * * * *